US008956626B2

(12) United States Patent
Moules et al.

(10) Patent No.: US 8,956,626 B2
(45) Date of Patent: Feb. 17, 2015

(54) MODIFIED VIRAL STRAINS AND METHOD FOR IMPROVING THE PRODUCTION OF VACCINE SEEDS OF INFLUENZA VIRUS

(75) Inventors: Vincent Moules, Lyons (FR); Manuel Rosa-Calatrava, Lyons (FR); Olivier Ferraris, Bron (FR); Matthieu Yver, Lyons (FR)

(73) Assignees: Universite Claude Bernard Lyon 1 (FR); Hospices Civils de Lyon (FR); Centre National de la Recherche Scientifique (CNRS) (FR)

(*) Notice: Subject to any disclaimer, the term of this patent is extended or adjusted under 35 U.S.C. 154(b) by 0 days.

(21) Appl. No.: 13/809,629

(22) PCT Filed: Jul. 8, 2011

(86) PCT No.: PCT/EP2011/061604
§ 371 (c)(1),
(2), (4) Date: Jan. 11, 2013

(87) PCT Pub. No.: WO2012/007380
PCT Pub. Date: Jan. 19, 2012

(65) Prior Publication Data
US 2013/0115242 A1    May 9, 2013

(51) Int. Cl.
A61K 39/145    (2006.01)
C07K 14/005    (2006.01)
C12N 7/00    (2006.01)
C12N 7/04    (2006.01)

(52) U.S. Cl.
CPC ............. *A61K 39/145* (2013.01); *C07K 14/005* (2013.01); *C12N 7/00* (2013.01); *C12N 2760/16121* (2013.01); *C12N 2760/16122* (2013.01); *C12N 2760/16134* (2013.01); *C12N 2760/16151* (2013.01)
USPC ...................................... 424/202.1; 424/93.1

(58) Field of Classification Search
CPC ........... C12N 2760/16162; C12N 2760/16261; C12N 2760/16121; C12N 2760/16161
See application file for complete search history.

(56) References Cited

U.S. PATENT DOCUMENTS 7,344,722 B1 *   3/2008   Maassab et al. ........... 424/206.1
7,758,868 B2 *   7/2010   Cameron et al. ........... 424/217.1
8,444,995 B2 *   5/2013   Soloff et al. ............... 424/185.1

FOREIGN PATENT DOCUMENTS

WO    WO2007091030 A2 *   8/2007

OTHER PUBLICATIONS

French Search Report issued from corresponding FR 1055716, dated Mar. 25, 2011.
International Search Report issued from corresponding PCT/EP2011/061604, dated Oct. 7, 2011.
Ferraris, Olivier, et al., "Evolution of the susceptibility to antiviral drugs of A/H3N2 influenza viruses isolated in France from 2002 to 2005," Jun. 8, 2006, pp. 6656-6658, Elsevier.
Lee, Kwang-Hee, et al., "The position 4 nucleotide at the 3' end of the influenza virus neuraminidase vRNA is involved in temporal regulation of transcription and replication of neuraminidase RNAs and affects the repertoire of influenza virus surface antigens," Journal of General Virology, 1998, pp. 1923-1934, vol. 79.
Moules, V., et al.,"Influenza Virion Morphologies Explained Bycellular Origin, Sub-types and Geneticbackground: Implications for Vaccine Design Andpathogenesis Studies," 4th European Congress of Virology—Abstracts, Apr. 7, 2010, pp. 86, European Society for Virology.
Wanitchang, Asawin et al., "Enhancement of Reverse Genetics-Derived Swine-Origin H1N1 Influenza Virus Seed Vaccine Growth by Inclusion of Indigenous Polymerase PB1 Protein," Virus Research, 2009, pp. 145-148, vol. 147.
GenBank HA: FJ888348.1, NA: CY038905.1, PB2: CY040177.1, PA: CY038908.1, NS: CY040174.1, PB1: CY040176.1, NP: CY040173.1 and M: CY040171.1.
GenBank CY040176.1, CY038909.1, CY038901.1, EF190980.1 and EF190972.1.
GenBank EU097800.
GenBank ACR08608.1.

* cited by examiner

*Primary Examiner* — Bao Li
(74) *Attorney, Agent, or Firm* — Banner & Witcoff, Ltd.

(57) ABSTRACT

Modified influenza A/PR/8/34 virus and reassortant influenza A/PR/8/34 virus including a modified PB1 gene and methods for improving the production of HA (hemagglutinin) and NA (neuraminidase) vaccine glycoproteins.

14 Claims, No Drawings

MODIFIED VIRAL STRAINS AND METHOD FOR IMPROVING THE PRODUCTION OF VACCINE SEEDS OF INFLUENZA VIRUS

RELATED APPLICATION DATA

This application is a National Stage Application under 35 U.S.C. 371 of co-pending PCT application PCT/EP2011/061604 designating the United States and filed Jul. 8, 2011; which claims the benefit of FR patent application number 1055716 and filed Jul. 13, 2010 each of which are hereby incorporated by reference in their entireties.

The present invention relates to modified influenza A/PR/8/34 viruses including a modified PB1 gene, and to methods implementing reassortant viruses having the genetic background of the modified A/PR/8/34 viruses for the production of vaccine seeds of influenza virus.

The flu, caused by influenza viruses, is a common viral respiratory infection observed throughout the world which evolves each winter through epidemic outbreaks in temperate regions. It remains today the second leading cause of infectious disease mortality after pneumonia. The influenza viruses responsible for pathology in man are the type A and type B influenza viruses. Whereas influenza B viruses circulate in the form of lineages, influenza A viruses are divided into virus subtypes according to the antigenic properties of the two major surface glycoproteins, hemagglutinin (HA) and neuraminidase (NA). Influenza viruses have between 300 and 700 glycoproteins on their surface with a theoretical NA/HA ratio of 1 to 10. The viruses that circulate in man and cause seasonal epidemics are the A (H1N1) and A (H3N2) viruses. Since the principal reservoir for influenza viruses is the animal reservoir (avian and porcine), animal viruses can cross the species barrier and infect man. Viruses such as the highly pathogenic avian influenza A (H5N1) virus and the pandemic A (H1N1) virus can create serious public health problems.

Vaccination is, at present, the only effective means for protecting populations from influenza viruses. The so-called seasonal vaccine provides immunity against the circulating seasonal A (H1N1) and A (H3N2) viruses and the B viruses. It is defined by the WHO each year based on the prototype strains of the previous year. The host's immune response is principally humoral with the synthesis of neutralizing antibodies which are directed against the HA and NA proteins. Due to the significant antigenic drift of these two proteins, in particular for the type A viruses, the composition of the vaccine must be revaluated annually.

The standard method for producing a vaccine rests first on obtaining, by genetic reassortment with the A/PR8/34 (H1N1) strain, vaccine seeds in eggs for each of the three prototype strains determined by the WHO. Most vaccine producers commonly use these reassortant viruses deriving principally from the parent A/PR/8/34 virus. Thus, each vaccine seed arises from a process of genetic reassortment between the prototype strain and the A/PR8/34 (H1N1) virus which has optimal replicative capacities in eggs.

The viral particle contains eight distinct genes composed of a single chain of RNA, each gene coding for one to three specific viral proteins: HA, NA, M1, M2, NP, NS1, NS2, PB1, PB1F2, PB1N40, PB2 and PA. Consequently, a long selection process makes it possible to obtain the vaccine reassortant, including at least the segments of genes coding for HA and NA of the prototype strain, on the genetic background of the PR8 virus ("6+2" composition). The three vaccine reassortants, stemming from genetic reassortment between the three prototype strains and the parent A/PR/8/34 strain, are then amplified in eggs. The HA and NA antigens are purified from products of an allantoic system, associated or not with adjuvants, in order to produce the doses of vaccine. This industrial process for producing vaccine doses is long (four to six months). Alternative strategies for obtaining doses of vaccine have been developed in recent years. Indeed, the use of cell lines to amplify vaccine reassortants makes it possible, among other things, to be no longer dependent on the "egg" system (insufficient quantity of eggs to manage a pandemic), to reduce the changes in surface antigens regularly observed using allantoic production methods, and to be non-allergenic. Today, however, few manufacturers have chosen this new production method because the industrial process does not at present perform as well as eggs perform.

In order reduce vaccine dose production time to a minimum, and with the objective of having an equivalent yield in terms of number of doses, vaccine seeds can be obtained by the use of reverse genetics techniques, making it possible to quickly obtain the vaccine reassortant with a "6+2" composition, thus eliminating all of the selection steps. The production of recombinant viruses by reverse genetics presents the most realistic alternative for responding effectively to the demand for vaccines. The production of recombinant viruses by reverse genetics opens the possibility, subsequently, of producing an "optimized" PR8 virus that makes it possible, when it is used by a process of genetic reassortment with prototype strains, to produce vaccine reassortants with viral characteristics optimized for the production of doses of vaccine in eggs or in cells.

In the current context of the emergence of a pandemic pathogenic virus, influenza infection could lead to 1.3 to 2 million hospitalizations and 280,000 to 650,000 deaths in the industrialized nations alone (WHO data).

The dose of vaccine is defined by a fixed quantity of HA antigen (15 µg per virus subtype per dose). Positive detection of the NA antigen is necessary to validate the lots of vaccine. One of the major economic issues is to be able to reduce the manufacturing costs of a dose of vaccine (more doses per production and/or reduction in the time to produce the same quantity of doses).

Wanitchang et al. describe improvement in the growth and an increase in the NA activity of a reassortant virus expressing the HA/NA glycoproteins of the H1N1 (S-OIV) virus when the PB1 gene of the reassortant ("5+3") A/PR/8/34 virus is replaced by the PB1 gene of the S-OIV virus. The improvement in growth and the increase in NA activity are, however, specific to S-OIV HA/NA glycoproteins. Furthermore, the improvement in growth and the increase in NA activity are not detected in a reassortant ("7+1") A/PR/8/34 virus including the S-OIV PB1 gene. This document does not describe methods for increasing the quantity of HA-NA glycoproteins on the surface of an A/PR/8/34 virus nor does it describe modified A/PR/8/34 viruses whose quantity of HA-NA glycoproteins on the surface of the virus is increased.

The present invention relates to viral strains (vaccine reassortants) that produce more surface glycoproteins and to methods for improving the production of HA/NA surface glycoproteins. The invention consists in particular of modifying the PR8 virus ordinarily used to produce vaccine seeds of influenza virus. This modification consists in the modification of certain amino acids of the PB1 protein in order to obtain vaccine reassortants with a greater quantity of surface glycoproteins (HA and NA) and a different HA/NA ratio in favor of NA. These constitute the antigens of the anti-influenza vaccine doses. The invention makes it possible to quantitatively and qualitatively optimize the vaccine seeds of influenza viruses type A and B.

One of the advantages of the invention is to increase the immunogenicity of the vaccine doses by the overexpression of NA in relation to a given quantity of HA produced.

Another advantage is to have available a system that makes it possible to increase the number of doses of vaccine produced in eggs or in cells by increasing the expression of surface glycoproteins.

SUMMARY OF THE INVENTION

The invention has as an object modified influenza A/PR/8/34 viruses, whose quantity of HA-NA (hemagglutinin and neuraminidase) glycoproteins on the surface is greater than 550 glycoproteins for a virion of 100 nm in diameter, including a mutated PB1 gene of SEQ ID NO: 1 coding for a PB1 protein having at least two specific amino acid modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

Preferably, the modified viruses according to the invention include a mutated PB1 gene of SEQ ID NO: 1 coding for a PB1 protein with at least modifications 563 (I→R) and 682 (V→I).

In another embodiment, the A/PR/8/34 viruses according to the invention include the PB1 gene of another influenza A virus strain whose quantity of HA-NA surface glycoproteins is greater than 550 glycoproteins for a virion of 100 nm in diameter.

Preferably, the modified influenza A/PR/8/34 viruses according to the invention include the PB1 gene of an H3N2 influenza virus having the sequence of SEQ ID NO: 2.

Advantageously, the modified influenza A/PR/8/34 viruses according to the invention are reassortant viruses including the HA and NA genes of another influenza virus.

In another advantageous embodiment, the modified influenza A/PR/8/34 viruses according to the invention include the HA and NA genes of an influenza virus selected from the viruses having the H3N2, H2N2, H1N2, H5N2, H5N1, H7N7, H9N2 and H3N1 subtypes.

Another object of the present invention is a method for producing HA-NA vaccine glycoproteins of influenza virus in which a modified influenza virus according to the invention including the HA and NA genes coding for said HA-NA vaccine glycoproteins is amplified in eggs or in cells.

Preferably, the HA-NA vaccine glycoproteins are selected from the glycoproteins of viruses having the H3N2, H2N2, H1N2, H5N2, H5N1, H7N7, H9N2 and H3N1 subtypes.

The invention also relates to a method for increasing the quantity of HA-NA glycoproteins on the surface of an influenza A/PR/8/34 virus, including the modification of the PB1 gene of SEQ ID NO: 1 of said influenza A/PR/8/34 virus in order to introduce into the PB1 protein coded by said PB1 gene at least two specific amino acid modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

Preferably, the method includes the modification of the PB1 gene of SEQ ID NO: 1 of said influenza A/PR/8/34 virus in order to introduce into the PB1 protein coded by said PB1 gene at least the two specific amino acid modifications 563 (I→R) and 682 (V→I).

In another embodiment, the method according to the invention includes the replacement of the PB1 gene of SEQ ID NO: 1 by the PB1 gene of another influenza A virus strain whose quantity of HA-NA surface glycoproteins is greater than 550 glycoproteins for a virion of 100 nm in diameter.

Preferably, the method includes the replacement of the PB1 gene of SEQ ID NO: 1 by the PB1 gene of an H3N2 influenza virus having the sequence of SEQ ID NO: 2.

Advantageously, the A/PR/8/34 virus is a reassortant virus including the HA and NA genes of another influenza virus.

In another advantageous embodiment, the A/PR/8/34 virus is a reassortant virus including the HA and NA genes of an influenza virus selected from the viruses having the H3N2, H2N2, H1N2, H5N2, H5N1, H7N7, H9N2 and H3N1 subtypes.

The invention also has as an object a method for increasing the immunogenicity of a dose of vaccine including HA-NA glycoproteins of influenza virus by raising the NA/HA ratio of the glycoproteins produced, wherein the glycoproteins are produced by amplification in eggs or in cells of a modified influenza virus according to the invention.

SEQUENCE LISTING

SEQ ID NO: 1: Protein sequence of PB1 of influenza A/PR8/8/34 A(H1N1) virus
SEQ ID NO: 2: Protein sequence of PB1 of influenza Moscow/10/99 A(H3N2) virus

DESCRIPTION OF THE INVENTION

The invention rests on the unexpected observation that different influenza virus strains do not have the same quantity of HA and NA glycoproteins on their surface. In particular, it has proven that the influenza viruses having the genetic background of the A/PR/8/34 parent strain, used by manufacturers for virus amplification by injection in fertilized chicken eggs, express a smaller quantity of HA and NA glycoproteins on their surface than other influenza virus strains. This observation has great importance because reassortant viruses having an A/PR/8/34 genetic background and expressing HA and NA vaccine glycoproteins are classically used for the production of anti-influenza vaccines. A dose of vaccine is defined by a fixed quantity of HA antigen of 15 µg per virus subtype per dose. Increasing the quantity of glycoproteins produced by influenza viruses having an A/PR/8/34 genetic background is a major issue in terms of improving vaccine dose production yields and reducing the manufacturing costs of these doses of vaccine.

In view of these results, it has now been found, unexpectedly, that the quantity of HA-NA glycoproteins produced by a virus having an A/PR/8/34 genetic background can be increased by genetic modification of the PB 1 gene of this virus. Thus, the present invention relates to modified viruses having an A/PR/8/34 genetic background and producing a larger quantity of HA-NA glycoproteins of prototype strains, to methods for increasing the production yield of HA-NA vaccine glycoproteins, and to methods for increasing the quantity of glycoproteins produced by an A/PR/8/34 virus. The present invention also relates to modified viruses with an A/PR/8/34 genetic background having a different HA/NA ratio in favor of NA.

The invention relates in particular to modified A/PR/8/34 viruses including a modified PB1 gene as well as to modified reassortant A/PR/8/34 viruses including a modified PB1 gene and the HA and NA genes of another virus and in particular of a prototype virus for producing HA/NA vaccine antigens. The invention also relates to methods for producing HA-NA glycoproteins including the amplification in eggs of the modified viruses or the reassortant viruses according to the invention.

Lastly, the invention also has as an object method for significantly increasing the quantity of HA-NA glycoproteins on the surface of an A/PR/8/34 virus or a reassortant virus having an A/PR/8/34 genetic background. These methods make it possible to improve the yield of HA-NA glycoprotein production.

The expression "influenza A/PR/8/34 virus" refers to viruses related to strain A/PR/8/34. Strain A/PR/8/34 results from adaptation to the production of influenza viruses in eggs, taken from a patient in Puerto Rico in 1934. Various clones of strain A/PR/8/34 have been developed and are well known to the person skilled in the art. Strain A/PR/8/34, as well as the various clones derived from this strain, has been the object of ATCC deposits. They are in particular ATCC deposits VR-95 and VR-1469. This A/PR/8/34 strain is used as the parent strain for the preparation of reassortant viruses having a high potential for multiplication in eggs for vaccine production. Various clones of strain A/PR/8/34 are used by manufacturers but these clones remain genetically very similar and are characterized by a high capacity for growth in eggs for vaccine production. The sequences of the eight gene segments of the A/PR/8/34 virus are available from GenBank under the following numbers (HA: FJ888348.1, NA: CY038905.1, PB2: CY040177.1, PA: CY038908.1, NS: CY040174.1, PB1: CY040176.1, NP: CY040173.1 and M: CY040171.1).

The expression "modified influenza A/PR/8/34 virus" refers to a virus related to strain A/PR/8/34 whose PB1 gene is modified.

Influenza A viruses include eight genes, most notably the PB1, HA and NA genes.

The expression "reassortant virus having the genetic background of the modified A/PR/8/34 virus" refers to a reassortant virus with six genes of the modified A/PR/8/34 virus, including the modified PB1 gene, and the genes coding for the HA and NA glycoproteins of another influenza virus strain. The genes coding for the HA and NA glycoproteins come in general from wild type influenza viruses (or prototype virus) which have been selected as being representative of large groups of influenza viruses on the basis of thorough antigenic and genetic studies (by WHO-associated laboratories). These wild-type influenza viruses (prototype virus) are grown directly from clinical samples. Thus, each year the WHO recommends preparing an anti-influenza vaccine from certain wild-type influenza viruses. The corresponding reassortant viruses having the genetic background of the modified A/PR/8/34 virus grow very well in eggs (characteristic of strain A/PR/8/34) and express HA and NA glycoproteins for the production of vaccine.

The terms "reassortant viruses" and "genetic reassortment" refer to a method by which the genes of two or several influenza viruses are found in different combinations, to yield hybrid viruses with the genes of each parent virus. This genetic reassortment can occur naturally or can be obtained in the laboratory.

The modified influenza A/PR/8/34 viruses according to the invention include a modified PB1 (polymerase basic protein 1) gene. The PB1 gene of influenza A viruses is well known to the person skilled in the art. The sequence of the A/PR/8/34 PB1 gene is, for example, available from GenBank under the numbers CY040176.1, CY038909.1, CY038901.1, EF190980.1 and EF190972.1.

The PB1 genes of various clones of influenza A/PR/8/34 virus may have a small number of sequence divergences even if the genetic drift for the PB 1 gene is small. In a particular embodiment, the PB1 gene of the influenza A/PR/8/34 virus codes for the PB1 protein of SEQ ID NO: 1. In another particular embodiment, the PB1 gene of the influenza A/PR/8/34 virus codes for the PB1 protein of SEQ ID NO: 1 or for a variant of this protein having at least 98%, 99% or 99.5% identity with SEQ ID NO: 1.

The expression "modified PB1 gene" refers to a PB1 gene including modifications of its sequence leading to a difference in the amino acid sequences of the proteins coded by this segment.

The PB1 gene codes for three proteins (PB1, PB and PB1N40), and the PB1 protein is well known and plays a central role in the replication/transcription of the virus (without this protein no replication occurs). The other proteins are termed auxiliary and are poorly understood. The PB1F2 protein seems to play a role in vivo whereas only one study describes a putative role in transcription for the PB 1N40 protein. Moreover, all of the PB 1 gene segments of circulating viruses do not code for the PB1F2 protein. The person skilled in the art will understand that modifications of the PB1 gene can thus lead to modifications of the PB1, PB1F2 and/or PB1N40 proteins.

A/PR/8/34 viruses including a modified PB1 gene are obtained by mutagenesis of the A/PR/8/34 PB 1 gene and in particular by the introduction of mutations into the sequence of the PB1 gene or by the replacement of the A/PR/8/34 PB1 gene by the PB1 gene of another influenza virus strain.

The term "HA-NA glycoproteins" refers to hemagglutinin (HA) glycoproteins and neuraminidase (NA) glycoproteins. These are specific antigenic proteins on the surface of influenza A viruses capable of inducing the production of neutralizing antibodies. Influenza A viruses are subdivided according to their combination of hemagglutinin and neuraminidase, with 16 HA subtypes and nine NA subtypes.

By virtue of the modification of their PB1 gene, the modified influenza A/PR/8/34 viruses and the reassortant influenza vaccine viruses including a genetic background of the modified A/PR/8/34 virus of the present invention have an increased quantity of HA-NA glycoproteins on their surface in relation to the quantity of HA-NA glycoproteins usually present on the surface of A/PR/8/34 viruses not including a modified PB1 gene.

Preferably, the quantity of HA-NA glycoproteins on the surface of A/PR/8/34 viruses including a modified PB1 gene is greater than 550, 600 and more preferentially 650 glycoproteins for a virion of 100 nm in diameter. The quantity of surface glycoproteins (HA+NA) is determined by measuring the distance between glycoprotein spikes and then is related to the surface area of a virus 100 nm in diameter. The distance between four glycoprotein spikes is measured by cryo-electron microscopy.

In preferred embodiments, the PB1 gene of strain A/PR/8/34 has modifications leading to the specific amino acid modifications in the PB1 protein. Preferably, the modification of the PB1 gene is accompanied by the specific modification of 1, 2, 3, 4, 5, 6, 7, 8, 9, 10, 11, 12, 13, 14 or 15 amino acids of the strain A/PR/3/84 PB1 protein. More preferentially, the modification of the PB1 gene is accompanied by the specific modification of at least two amino acids of the strain A/PR/3/84 PB 1 protein.

Preferably, the modified PB1 gene codes for a PB1 protein including at least 1, 2, 3, 4, 5, 6, 7, 8, 9, 10, 11, 12, 13, 14 or 15 modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

In an advantageous embodiment of the invention, the modified PB1 gene codes for a PB1 protein with at least modifications 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

More preferentially, the modified PB1 gene codes for a PB1 protein with at least two modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

Advantageously, the modified PB1 gene codes for a protein with at least modifications 563 (I→R) and 682 (V→I).

In other embodiments, the PB1 gene of the A/PR/8/34 virus is replaced by the PB1 gene of another influenza virus strain whose quantity of HA-NA surface glycoproteins is greater than 550, 600 or 650 glycoproteins for a virion of 100 nm in diameter.

In an advantageous embodiment, the PB1 gene of the A/PR/8/34 virus is replaced by a gene coding for the PB1 protein of SEQ ID NO: 2.

The invention also relates to reassortant influenza viruses having the genetic background of a modified influenza A/PR/8/34 virus according to the invention and including the HA and NA genes of another influenza virus. These reassortant viruses thus typically carry six genes of the modified A/PR/8/34 virus (including the modified PB1 gene) and two genes of another influenza virus strain, the genes coding for the HA and NA glycoproteins. The reassortant viruses of the present invention grow very well in eggs as do strain A/PR/8/34 viruses while producing more HA and NA glycoproteins on their surface. Thus, with the same quantity of reassortant virus produced, it is possible to produce more doses of vaccine.

Preferably, the genes coding for the HA and NA glycoproteins come from virus type A and advantageously wild influenza viruses (prototype virus). Advantageously, the genes coding for the HA and NA glycoproteins come from circulating human or animal influenza viruses regardless of virus subtype. In preferred embodiments, the genes coding for the HA and NA glycoproteins come from influenza viruses selected from the viruses having the H3N2, H2N2, H1N2, H5N2, H5N1, H7N7, H9N2 and H3N1 subtypes.

In certain embodiments, the invention relates to reassortant influenza viruses including five genes of the A/PR/8/34 virus and the PB1, HA and NA genes of one or more other influenza virus strains. Preferably, the PB1 gene of the A/PR/8/34 virus is replaced by the PB1 gene of another influenza virus strain whose quantity of HA-NA surface glycoproteins is greater than 550, 600 or 650 glycoproteins for a virion of 100 nm in diameter. Advantageously, the PB1 gene of the A/PR/8/34 virus is replaced by a gene coding for the PB1 protein of SEQ ID NO: 2.

The invention also relates to methods implementing the modified A/PR/8/34 viruses and the reassortant viruses having the genetic background of the modified A/PR/8/34 virus for the production of HA-NA glycoproteins.

The modified A/PR/8/34 viruses according to the invention and the reassortant viruses obtained with the modified A/PR/8/34 viruses are particularly suited to the production of vaccine seeds by amplification in fertilized chicken eggs or in cells.

The reassortant viruses having the genetic background of the A/PR/8/34 virus (six A/PR/8/34 genes including the modified PB1 gene) and the HA and NA genes of a wild-type virus (or prototype virus) are particularly suited to the production of HA-NA vaccine glycoproteins. The reassortant viruses are amplified in fertilized chicken eggs or in cells according to standard techniques.

In advantageous embodiments, the invention relates to methods for producing HA-NA vaccine glycoproteins of influenza virus in which a reassortant virus having the genetic background of a modified influenza A/PR/8/34 virus according to the invention and including the HA and NA genes coding for said HA-NA vaccine glycoproteins is amplified in eggs or in cells.

Preferably, the HA-NA vaccine glycoproteins are selected from the HA-NA glycoproteins of influenza A virus and more particularly from the HA-NA glycoproteins of circulating human or animal influenza regardless of virus subtype. In preferred embodiments, the HA and NA vaccine glycoproteins are selected from the H3N2, H2N2, H1N2, H5N2, H5N1, H7N7, H9N2 and H3N1 subtypes.

The invention also relates to the HA-NA glycoproteins obtained by these methods.

The invention also relates to methods for increasing the quantity of HA-NA glycoproteins on the surface of an influenza A/PR/8/34 virus or a reassortant A/PR/8/34 virus including the modification of the PB1 gene of this virus.

These modifications of the PB1 gene are described above.

The increase in the quantity of HA-NA glycoproteins is measured in relation to the quantity of glycoproteins present on the surface of an A/PR/8/34 virus or a reassortant A/PR/8/34 virus not including a modified PB1 gene.

In advantageous embodiments, this increase makes it possible to obtain A/PR/8/34 viruses or reassortant A/PR/8/34 viruses whose quantity of HA-NA surface glycoproteins is greater than 550, 600 or 650 glycoproteins for a virion of 100 nm in diameter.

Preferably, this modification includes the modification of the PB 1 gene of said influenza A/PR/8/34 virus or said reassortant influenza A/PR/8/34 virus in order to introduce into the PB1 protein coded by said PB1 gene at least 1, 2, 3, 4, 5, 6, 7, 8, 9, 10, 11, 12, 13, 14 or 15 specific amino acid modifications.

More preferentially, this modification includes the modification of the PB1 gene of said influenza A/PR/8/34 virus or said reassortant influenza A/PR/8/34 virus in order to introduce into the PB1 protein coded by said PB1 gene at least 1, 2, 3, 4, 5, 6, 7, 8, 9, 10, 11, 12, 13, 14 or 15 specific amino acid modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

Advantageously, this modification includes the modification of the PB1 gene of said influenza A/PR/8/34 virus or said reassortant influenza A/PR/8/34 virus in order to introduce into the PB1 protein coded by said PB1 gene at least the specific amino acid modifications 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

Advantageously, this modification includes the modification of the PB1 gene of said influenza A/PR/8/34 virus or said reassortant influenza A/PR/8/34 virus in order to introduce into the PB1 protein coded by said PB1 gene at least two specific amino acid modifications selected from 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

More advantageously, this modification includes the modification of the PB1 gene of said influenza A/PR/8/34 virus or said reassortant influenza A/PR/8/34 virus in order to introduce into the PB1 protein coded by said PB1 gene at least the two specific amino acid modifications 563 (I→R) and 682 (V→I).

In other embodiments, the modification of the PB 1 gene of said influenza A/PR/8/34 virus or said reassortant influenza A/PR/8/34 virus includes the replacement of the PB1 gene of the influenza A/PR/8/34 virus by the PB1 gene of another influenza virus whose quantity of HA-NA surface glycoproteins is greater than 550, 600 or 650 glycoproteins for a virion of 100 nm in diameter.

Preferably, the modification of the PB1 gene of said influenza A/PR/8/34 virus or said reassortant influenza A/PR/8/34 virus includes the replacement of the PB1 gene of the influenza A/PR/8/34 virus by the PB1 gene of SEQ ID NO: 2.

The invention also relates to methods for improving the production yield of HA-NA vaccine glycoproteins of influenza virus by amplification in eggs or in cells of a reassortant vaccine virus having an A/PR/8/34 genetic background in which the quantity of HA-NA glycoproteins on the surface of said reassortant virus is increased by the modification of the A/PR/8/34 PB 1 gene.

The invention also relates to a method for preparing a reassortant vaccine virus for the production of HA-NA vaccine glycoproteins in which six genes of a modified A/PR/8/34 virus according to the invention are combined with two genes coding for the HA and NA vaccine glycoproteins of a prototype influenza virus (wild-type virus).

One of the advantages of the invention is to increase the immunogenicity of vaccine doses by the overexpression of NA in relation to a fixed quantity of HA produced.

Thus, the invention also relates to a method for increasing the immunogenicity of a dose of vaccine including HA-NA glycoproteins of influenza virus by raising the NA/HA ratio of the glycoproteins produced, in which the glycoproteins are produced by amplification in eggs or in cells of a reassortant virus having the genetic background of a modified A/PR/8/34 virus according to the invention.

EXAMPLES

Example 1

Production of Recombinant Viruses by Reverse Genetics

We produced nine recombinant viruses by reverse genetics according to the protocol developed in our laboratory. The genomic compositions of the recombinant viruses are as follows (Table 1):

Virus H3N2 A/Moscow/10/99 (MO)
Virus H1N1 A/PR/8/34 (PR8)
Virus A: "Classic" PR8 vaccine reassortant including segments of the HA and NA genes of MO on the genetic background of PR8 virus
Virus B: PR8 vaccine reassortant including segments of the HA, NA and PB1 genes of MO on the genetic background of PR8 virus.
Virus C: PR8 including a segment of the PB1 gene of MO
Virus D: "Classic" PR8 vaccine reassortant including segments of the HA and NA genes of avian influenza H5N2 A/Finch/England/2051/91 (Virus FI)
Virus E: PR8 vaccine reassortant including segments of the HA and NA genes of FI and a segment of PB 1 gene of MO on the genetic background of PR8 virus
Virus F: "Classic" PR8 vaccine reassortant including segments of the HA and NA genes of human H3N2 virus A/California/10/04 (Virus CAL)
Virus G: PR8 vaccine reassortant including segments of the HA and NA genes of CAL and a segment of PB 1 gene of MO on the genetic background of PR8 virus The production of recombinant virus in vitro rests on the transfection of 293T cells with eight plasmids each including a segment of gene. Production of the viruses was carried out in the laboratory with its own molecular and cellular tools. The production yields obtained for the nine recombinant viruses are similar in cells and conform to the normal production of recombinant viruses.

TABLE 1

Genomic composition of the recombinant viruses produced by reverse genetics

| Virus | HA | NA | M | NS | PB1 | PB2 | PA | NP |
|---|---|---|---|---|---|---|---|---|
| PR8 | PR8 | PR8 | PR8 | PR8 | PR8 | PR8 | PR8 | PR8 |
| MO | MO | MO | MO | MO | MO | MO | MO | MO |
| A | MO | MO | PR8 | PR8 | PR8 | PR8 | PR8 | PR8 |
| B | MO | MO | PR8 | PR8 | MO | PR8 | PR8 | PR8 |
| C | PR8 | PR8 | PR8 | PR8 | MO | PR8 | PR8 | PR8 |
| D | FI | FI | PR8 | PR8 | PR8 | PR8 | PR8 | PR8 |
| E | FI | FI | PR8 | PR8 | MO | PR8 | PR8 | PR8 |
| F | CAL | CAL | PR8 | PR8 | PR8 | PR8 | PR8 | PR8 |
| G | CAL | CAL | PR8 | PR8 | MO | PR8 | PR8 | PR8 |

PR8: A/Puerto Rico/10/34 H1N1
MO: A/Moscow/10/99 H3N2
FI: A/Finch/England/2051/91
CAL: A/California/10/04 H3N2

Example 2

Comparative Analysis of HA-NA Glycoprotein Density on the Surface of Recombinant Viruses by Cryo-Electron Microscopy (Table 2)

The various viruses produced by reverse genetics are amplified and purified on a sucrose cushion. The purified viruses deposited on a grid are frozen at very low temperature and observed by low-temperature electron microscopy.

The density of the surface glycoproteins (GP) is determined by measuring the distance between four glycoprotein spikes (ImageJ image analysis software) and is related to the surface of a virus 100 nm in diameter according to the following formula: $4\pi R^2$, with R=50 nm.

Results:

Virus PR8: 500 GPs on the surface of a virus 100 nm in diameter.
Virus MO: 689 GPs on the surface of a virus 100 nm in diameter.
Virus A: 500 GPs on the surface of a virus 100 nm in diameter.
Virus B: 700 GPs on the surface of a virus 100 nm in diameter.
Virus C: 598 GPs on the surface of a virus 100 nm in diameter.
Virus D: 498 GPs on the surface of a virus 100 nm in diameter.
Virus E: 640 GPs on the surface of a virus 100 nm in diameter.
Virus F: 502 GPs on the surface of a virus 100 nm in diameter.
Virus G: 703 GPs on the surface of a virus 100 nm in diameter.

TABLE 2

Quantity of glycoproteins (GP) and NA enzyme activity

| Virus | Quantity of GP/100 nm virus | NA activity (RFU/10E5 viruses) |
|---|---|---|
| PR8 | 500 | 14234 |
| MO | 689 | 29340 |
| A | 500 | 14600 |
| B | 700 | 64000 |
| C | 598 | 63540 |
| D | 498 | 8450 |
| E | 640 | 36542 |
| F | 502 | 13897 |
| G | 703 | 63470 |

There is a significant difference in terms of quantity of glycoproteins between the recombinant PR8 H1N1 virus and the recombinant MO H3N2 virus (+35% for the H3N2 virus).

Recombinant virus A, corresponding to a classic vaccine composition, has a quantity of GP similar to the PR8 virus.

Recombinant virus B (including the MO PB 1 gene) has a quantity of GP on its surface identical to that observed for the MO virus.

The PB1 gene makes it possible to obtain recombinant vaccine viruses including a quantity of GP equal to 700 GP per virion of 100 nm in diameter.

Recombinant virus C has a greater quantity of GP on its surface than that observed for virus PR8 (20%).

The increase in the quantity of GP due to the segment of MO PB 1 gene was found for recombinant viruses F and G with H3N2 GP of the CAL strain on their surfaces.

The increase in the quantity of GP mediated by the segment of MO PB 1 gene was observed for reassortant vaccine viruses with avian GP of the FI H5N2 virus (viruses D and E).

Example 3

Determination and Comparison of Neuraminidase (NA) Activity of the Recombinant Viruses (Table 2)

NA activity was determined using an experimental protocol developed by the laboratory (Ferraris et al. Vaccine 2006). Since NA activity is determined for a given quantity of virus (RFUs for $10^{E}5$ viruses), the variations observed reflect the quantity of NA proteins on the surface of the viruses (for identical NA).

The variations in NA RFU activities (for the viruses including human N2 neuraminidase) are indicated below:
MO: 29340 RFUs for 10E5 viruses
Virus A: 14600 RFUs for 10E5 viruses
Virus B: 58000 RFUs for 10E5 viruses
Virus F: 13897 RFUs for 10E5 viruses
Virus G: 63470 RFUs for 10E5 viruses.

An increase in the quantity of NA is observed for recombinant viruses B and G in relation to recombinant viruses A and F, which are classic reassortant vaccine viruses.

The variations in NA RFU activities (for the viruses including avian N2 neuraminidase) are indicated below:
Virus D: 8450 RFUs for 10E5 viruses
Virus E: 36542 RFUs for 10E5 viruses.

An increase in the quantity of NA is observed for recombinant virus E (segment of the MO PB1 gene) in relation to recombinant virus D, which is a classic reassortant vaccine virus.

The variations in NA RFU activities (for the viruses including N1 neuraminidase) are indicated below:
Virus PR8: 14234 RFUs for 10E5 viruses
Virus C: 63540 RFUs for 10E5 viruses.

An increase in the quantity of NA is observed for recombinant virus C (segment of MO PB 1 gene) in relation to virus PR8.

In conclusion, the classic reassortant vaccine virus including the PB1 gene of the MO virus has greater NA enzyme activity than that measured for the classic vaccine reassortant.

The introduction of the MO virus PB1 gene into the genetic background of the classic reassortant vaccine virus makes it possible to:
- increase the number of GP on the surface of the viruses (+20% to +35%),
- increase the number of NA on the surface of the viruses (increase in NA activity).

Example 4

Determination of the Specific H3N2 PB1 Sequences Responsible for the Properties Presented Above, by Comparison with Amino Acid Sequences Between the PR8 H1N1 and MO H3N2 Viruses Alignment of the protein sequences of the PB1 proteins shows a difference of 30 amino acids between PR8 and MO.

A strategy of directed mutagenesis making it possible to modify the protein sequence of the PR8 PB 1 protein in order to obtain the protein sequence of the MO PB 1 protein made it possible to demonstrate a list of mutations which is the object of the present patent application. List of mutations: 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K).

A more refined experimental strategy made it possible to identify two mutations involved in the biological process described. The introduction of mutations I563R and V682I into the PR8 (virus A) PB 1 protein makes it possible to obtain a phenotype (quantity of GP and NA activity) similar to that observed for virus B.

REFERENCES

Ferraris, O., Kessler, N., Valette, M., Lina, B., 2006, Evolution of the susceptibility to antiviral drugs of A/H3N2 influenza viruses isolated in France from 2002 to 2005. Vaccine 24, 6656-6659

Wanitchang et al., Virus Research, 147, 145-148, 2010

The invention claimed is:

1. A modified influenza A/PR/8/34 virus, whose quantity of HA-NA (hemagglutinin and neuraminidase) glycoproteins on the surface is greater than 550 glycoproteins for a virion of 100 nm in diameter, including a mutated PB1 gene of SEQ ID NO: 1 coding for a PB1 protein having at least two specific amino acid modifications selected from the group consisting of: 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K), wherein the modified influenza A/PR/8/34 virus is reassortant including the HA and NA genes of another influenza virus.

2. The modified influenza A/PR/8/34 virus according to claim 1, wherein it includes a mutated PB1 gene of SEQ ID NO: 1 coding for a PB1 protein with at least both amino acid modifications 563 (I→R) and 682 (V→I).

3. The modified influenza A/PR/8/34 virus according to claim 1, wherein it includes the PB1 gene of another strain of influenza A virus whose quantity of HA-NA surface glycoproteins is greater than 550 glycoproteins for a virion of 100 nm in diameter.

4. The modified influenza A/PR/8/34 virus according to claim 1, wherein it includes the PB1 gene of H3N2 influenza virus having the sequence of SEQ ID NO: 2.

5. The modified influenza A/PR/8/34 virus according to claim 1, including the HA and NA genes of an influenza virus selected from the viruses having the H3N2, H2N2, H1N2, H5N2, H5N1, H7N7, H9N2 and H3N1 subtypes.

6. A method for producing HA-NA vaccine glycoproteins of influenza virus, wherein a modified influenza virus according to claim 1 including the HA and NA genes coding for said HA-NA vaccine glycoproteins is amplified in eggs or in cells.

7. The method for producing HA-NA vaccine glycoproteins of influenza virus according to claim 6, wherein the HA-NA vaccine glycoproteins are selected from the glycoproteins of viruses having the H3N2, H2N2, H1N2, H5N2, H5N1, H7N7, H9N2 and H3N1 subtypes.

8. A method for increasing the quantity of HA-NA glycoproteins on the surface of an influenza A/PR/8/34 virus, wherein it includes the modification of the PB1 gene of SEQ ID NO: 1 of said influenza A/PR/8/34 virus in order to introduce into the PB1 protein coded by said PB1 gene at least two specific amino acid modifications selected from the group consisting of: 188 (K→E), 205 (M→I), 212 (L→V), 216 (S→G), 398 (E→D), 486 (R→K), 563 (I→R), 576 (I→L), 581 (E→D), 584 (R→Q), 586 (K→R), 617 (D→N), 621 (Q→R), 682 (V→I) and 691 (R→K), wherein the influenza A/PR/8/34 virus is reassortant including the HA and NA genes of another influenza virus.

9. The method for increasing the quantity of HA-NA glycoproteins on the surface of an influenza A/PR/8/34 virus according to claim 8, wherein it includes the modification of the PB1 gene of SEQ ID NO: 1 of said influenza A/PR/8/34 virus in order to introduce into the PB1 protein coded by said PB1 gene at least the two specific amino acid modifications 563 (I→R) and 682 (V→I).

10. The method for increasing the quantity of HA-NA glycoproteins on the surface of an influenza A/PR/8/34 virus according to claim 8, wherein it includes the replacement of the PB1 gene of SEQ ID NO: 1 by the PB1 gene of another influenza A virus strain whose quantity of HA-NA surface glycoproteins is greater than 550 glycoproteins for a virion of 100 nm in diameter.

11. The method for increasing the quantity of HA-NA glycoproteins on the surface of an influenza A/PR/8/34 virus according to claim 10, wherein it includes the replacement of the PB1 gene of SEQ ID NO: 1 by the PB1 gene of an H3N2 influenza virus having the sequence of SEQ ID NO: 2.

12. The method for increasing the quantity of HA-NA glycoproteins on the surface of an influenza A/PR/8/34 virus according to claim 1, wherein the A/PR/8/34 virus is a reassortant virus including the HA and NA genes of an influenza virus selected from the viruses having the H3N2, H2N2, H1N2, H5N2, H5N1, H7N7, H9N2 and H3N1 subtypes.

13. A method for increasing the immunogenicity of a dose of vaccine including HA-NA glycoproteins of influenza virus by raising the NA/HA ratio of the glycoproteins produced, wherein the glycoproteins are produced by amplification in eggs or in cells of a modified influenza virus according to claim 1.

14. A method for increasing the immunogenicity of a dose of vaccine including HA-NA glycoproteins of influenza virus by raising the NA/HA ratio of the glycoproteins produced, wherein the glycoproteins are produced by amplification in eggs or in cells of a modified influenza virus according to claim 5.

* * * * *

UNITED STATES PATENT AND TRADEMARK OFFICE
CERTIFICATE OF CORRECTION

PATENT NO. : 8,956,626 B2
APPLICATION NO. : 13/809629
DATED : February 17, 2015
INVENTOR(S) : Vincent Moules et al.

It is certified that error appears in the above-identified patent and that said Letters Patent is hereby corrected as shown below:

Title Page, in Item (30) Foreign Application Priority Data:

Should read -- FRANCE 1055716 07/13/2010 --

Signed and Sealed this
Eleventh Day of August, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 757
<212> TYPE: PRT
<213> ORGANISM: Influenza A virus -continued

```
<400> SEQUENCE: 1

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415
```

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
            450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Ile Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755

<210> SEQ ID NO 2
<211> LENGTH: 757
<212> TYPE: PRT
<213> ORGANISM: Influenza A virus

<400> SEQUENCE: 2

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His

```
            20                  25                  30
Gly Thr Gly Thr Gly Tyr Thr Met Asp Thr Val Asn Arg Thr His Gln
            35                  40                  45
Tyr Ser Glu Lys Gly Lys Trp Thr Thr Asn Thr Glu Thr Gly Ala Pro
 50                  55                  60
Gln Leu Asn Pro Ile Asp Gly Pro Leu Pro Glu Asp Asn Glu Pro Ser
 65                  70                  75                  80
Gly Tyr Ala Gln Thr Asp Cys Val Leu Glu Ala Met Ala Phe Leu Glu
                 85                  90                  95
Glu Ser His Pro Gly Ile Phe Glu Asn Ser Cys Leu Glu Thr Met Glu
                100                 105                 110
Val Val Gln Gln Thr Arg Val Asp Lys Leu Thr Gln Gly Arg Gln Thr
                115                 120                 125
Tyr Asp Trp Thr Leu Asn Arg Asn Gln Pro Ala Ala Thr Ala Leu Ala
                130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Met Glu Ser Met Asp Lys
                165                 170                 175
Glu Glu Met Glu Ile Thr Thr His Phe Gln Arg Glu Arg Arg Val Arg
                180                 185                 190
Asp Asn Met Thr Lys Lys Met Val Thr Gln Arg Thr Ile Gly Lys Lys
                195                 200                 205
Lys Gln Arg Val Asn Lys Arg Gly Tyr Leu Ile Arg Ala Leu Thr Leu
                210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Ser Ile Cys Glu Lys Leu Glu Gln Ser Gly Leu Pro
                260                 265                 270
Val Gly Gly Asn Glu Lys Lys Ala Lys Leu Ala Asn Val Val Arg Lys
                275                 280                 285
Met Met Thr Asn Ser Gln Asp Thr Glu Leu Ser Phe Thr Ile Thr Gly
                290                 295                 300
Asp Asn Thr Lys Trp Asn Glu Asn Gln Asn Pro Arg Met Phe Leu Ala
305                 310                 315                 320
Met Ile Thr Tyr Ile Thr Lys Asn Gln Pro Glu Trp Phe Arg Asn Ile
                325                 330                 335
Leu Ser Ile Ala Pro Ile Met Phe Ser Asn Lys Met Ala Arg Leu Gly
                340                 345                 350
Lys Gly Tyr Met Phe Glu Ser Lys Arg Met Lys Leu Arg Thr Gln Ile
                355                 360                 365
Pro Ala Glu Met Leu Ala Ser Ile Asp Leu Lys Tyr Phe Asn Glu Ser
                370                 375                 380
Thr Arg Lys Lys Ile Glu Lys Ile Arg Pro Leu Leu Ile Asp Gly Thr
385                 390                 395                 400
Ala Ser Leu Ser Pro Gly Met Met Met Gly Met Phe Asn Met Leu Ser
                405                 410                 415
Thr Val Leu Gly Val Ser Ile Leu Asn Leu Gly Gln Lys Lys Tyr Thr
                420                 425                 430
Lys Thr Thr Tyr Trp Trp Asp Gly Leu Gln Ser Ser Asp Asp Phe Ala
                435                 440                 445
```

```
Leu Ile Val Asn Ala Pro Asn His Glu Gly Ile Gln Ala Gly Val Asp
        450             455             460
Arg Phe Tyr Arg Thr Cys Lys Leu Val Gly Ile Asn Met Ser Lys Lys
465             470             475             480
Lys Ser Tyr Ile Asn Lys Thr Gly Thr Phe Glu Phe Thr Ser Phe Phe
            485             490             495
Tyr Arg Tyr Gly Phe Val Ala Asn Phe Ser Met Glu Leu Pro Ser Phe
            500             505             510
Gly Val Ser Gly Ile Asn Glu Ser Ala Asp Met Ser Ile Gly Val Thr
            515             520             525
Val Ile Lys Asn Asn Met Ile Asn Asn Asp Leu Gly Pro Ala Thr Ala
        530             535             540
Gln Met Ala Leu Gln Leu Phe Ile Lys Asp Tyr Arg Tyr Thr Tyr Arg
545             550             555             560
Cys His Arg Gly Asp Thr Gln Ile Gln Thr Arg Arg Ser Phe Glu Leu
            565             570             575
Lys Lys Leu Trp Asp Gln Thr Gln Ser Arg Ala Gly Leu Leu Val Ser
            580             585             590
Asp Gly Gly Pro Asn Leu Tyr Asn Ile Arg Asn Leu His Ile Pro Glu
            595             600             605
Val Cys Leu Lys Trp Glu Leu Met Asn Glu Asp Tyr Arg Gly Arg Leu
        610             615             620
Cys Asn Pro Leu Asn Pro Phe Val Ser His Lys Glu Ile Glu Ser Val
625             630             635             640
Asn Asn Ala Val Val Met Pro Ala His Gly Pro Ala Lys Ser Met Glu
            645             650             655
Tyr Asp Ala Val Ala Thr Thr His Ser Trp Ile Pro Lys Arg Asn Arg
            660             665             670
Ser Ile Leu Asn Thr Ser Gln Arg Gly Ile Leu Glu Asp Glu Gln Met
            675             680             685
Tyr Gln Lys Cys Cys Asn Leu Phe Glu Lys Phe Phe Pro Ser Ser Ser
690             695             700
Tyr Arg Arg Pro Val Gly Ile Ser Ser Met Val Glu Ala Met Val Ser
705             710             715             720
Arg Ala Arg Ile Asp Ala Arg Ile Asp Phe Glu Ser Gly Arg Ile Lys
            725             730             735
Lys Glu Glu Phe Ser Glu Ile Met Lys Ile Cys Ser Thr Ile Glu Glu
            740             745             750
Leu Arg Arg Gln Lys
            755
```